United States Patent
Näfe et al.

(10) Patent No.: US 6,645,548 B1
(45) Date of Patent: Nov. 11, 2003

(54) METHOD FOR PRODUCING A REFERENCE ELECTRODE FOR A GALVANIC CELL WITH CATION-CONDUCTING SOLID ELECTROLYTES

(75) Inventors: Helfried Näfe, Stuttgart (DE); Stephanie Gollhofer, Fellbach (DE); Fritz Aldinger, Leinfelden-Echterdingen (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 09/743,167
(22) PCT Filed: Sep. 9, 1999
(86) PCT No.: PCT/EP99/06673
§ 371 (c)(1),
(2), (4) Date: Jan. 5, 2001
(87) PCT Pub. No.: WO00/16080
PCT Pub. Date: Mar. 23, 2000

(30) Foreign Application Priority Data

Sep. 11, 1998 (DE) .......................................... 198 41 707

(51) Int. Cl.⁷ ................................................. B05D 5/12
(52) U.S. Cl. ........................ 427/58; 427/115; 427/126.3
(58) Field of Search ......................... 427/58, 115, 126.3

(56) References Cited

U.S. PATENT DOCUMENTS

| | | | | |
|---|---|---|---|---|
| 5,114,803 A | * | 5/1992 | Ishihara et al. | ................ 429/30 |
| 5,552,086 A | * | 9/1996 | Siiman et al. | ............ 252/315.2 |
| 5,707,763 A | * | 1/1998 | Shimizu et al. | ............. 429/217 |
| 6,156,453 A | * | 12/2000 | Shimizu et al. | ............. 429/212 |

FOREIGN PATENT DOCUMENTS

| | | |
|---|---|---|
| DE | 195 03 783 | 8/1996 |
| GB | 2 046 502 | 11/1980 |

* cited by examiner

*Primary Examiner*—Bret Chen
(74) *Attorney, Agent, or Firm*—Fulbright & Jaworski L.L.P.

(57) ABSTRACT

To produce reference electrodes for galvanic cells having solid electrolytes, comprising metal oxides or/and double oxides, at least one oxide or double oxide is prepared as a hydrosol or organosol and applied in liquid form to the electrolyte to form a solid film. Preferably, a double oxide $Me^1_x Me^2_y O_z$ and (i) a metal oxide $Me^2_m O_n$ or (ii) a double oxide $Me^1_a Me^2_b O_c$ with a lower $Me^1$ content are present in the reference electrode material.

4 Claims, 2 Drawing Sheets

Figure 1:
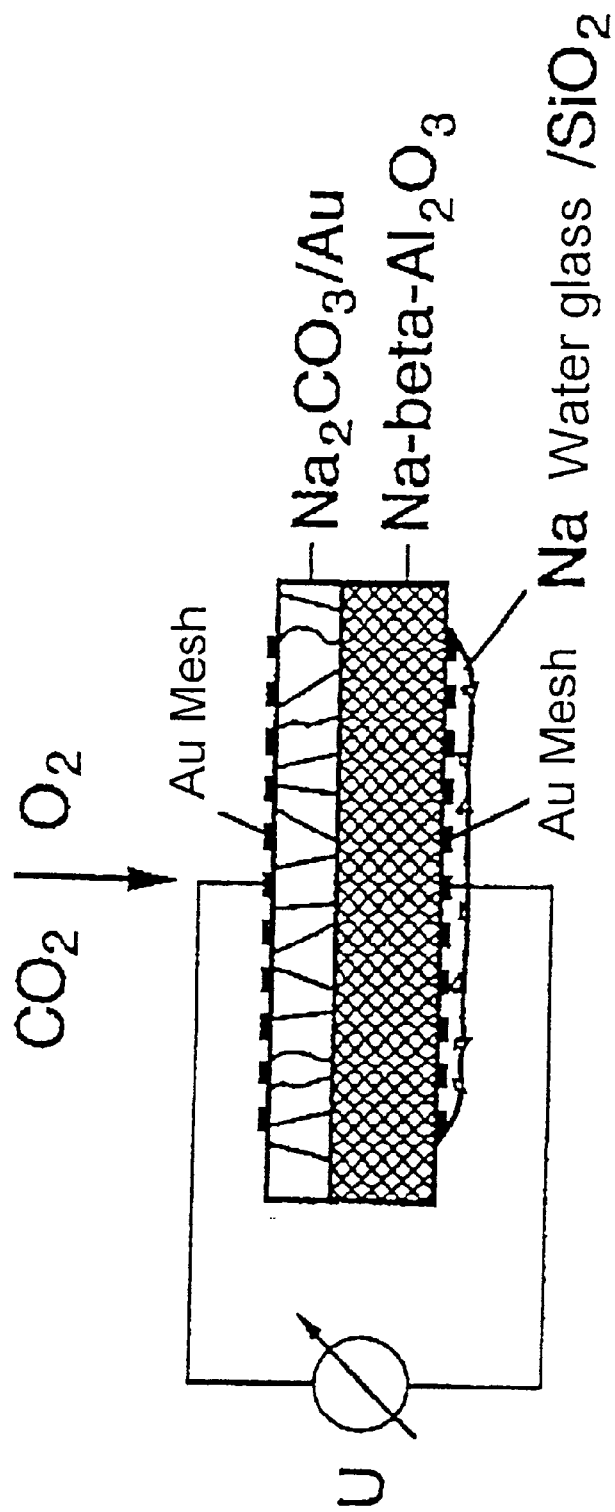

METHOD FOR PRODUCING A REFERENCE ELECTRODE FOR A GALVANIC CELL WITH CATION-CONDUCTING SOLID ELECTROLYTES

FIELD OF APPLICATION OF THE INVENTION

The invention relates to the way of producing a reference electrode for a galvanic cell having e.g. a lithium-, sodium- or potassium-ion-conducting solid electrolyte and being of the type as used for potentiometric sensors for detecting $CO_2$, $SO_x$ and $NO_x$.

Characteristics of the Solutions Known in the Art

Already known is a series of reference electrodes for sodium-ion-conducting solid electrolytes whose chemical potential results from the equilibrium between an $Na_2O$-containing double oxide in the form $Na_xMe_yO_z$ and, on the other hand, (i) the respective oxide $Me_mO_n$ or (ii) a double oxide $Na_aMe_bO_c$ with a lower $Na_2O$ content:

| (i) $Na^+$ solid electrolyte | $\|$ $Na_xMe_yO_z$, $Me_mO_n$ | $\|$ $O_2$, noble metal |
|---|---|---|
| (ii) $Na^+$ solid electrolyte | $\|$ $Na_xMe_yO_z$, $Na_aMe_bO_c$ | $\|$ $O_2$, noble metal |
|  | II | I |

In these systems, the sodium potential establishes itself as a result of the following relationships:

(i) $Na_xMe_yO_z \equiv x\,Na + \dfrac{x}{4}\,O_2 + q\,Me_mO_n$ ($y = qm$, $z = cn + x/2$)

(ii) $Na_xMe_yO_z \equiv$ $(x-a)Na + \dfrac{x-a}{4}\,O_2 + Na_aMe_bO_c$ ($y = b$, $z = c + (x-a)/2$)

On this basis, the Na potential, assuming that the oxides involved in the equilibrium coexist in pure form in each case, is defined as follows:

(i) $\ln a_{Na} = \dfrac{\Delta_f G^o_{Na_xMe_yO_z} - q \cdot \Delta_f G^o_{Me_mO_n}}{x\,RT} - \dfrac{1}{4}\ln PO_2$ (1a)

(ii) $\ln a_{Na} = \dfrac{\Delta_f G^o_{Na_xMe_yO_z} - c \cdot \Delta_f G^o_{Na_aMe_bO_c}}{(x-a)\,RT} - \dfrac{1}{4}\ln PO_2$ (1b)

where $\Delta_f G^*_{Na_xMe_yO_z}$, $\Delta_f G^*_{Na_aMe_bO_c}$ and $\Delta_f G^*_{Me_mO_n}$ are the free standard enthalpies of formation of the oxides involved. The sodium potential is therefore at all times a defined function of just the ambient temperature and the ambient oxygen partial pressure. As the measuring electrodes in a series of gas sensors are of similar structure and therefore likewise are oxygen-pressure-dependent, the output signal of the complete sensor ultimately becomes independent of the oxygen potential in the ambient gas atmosphere.

Examples of said cases are inter alia: (i) $NaAl_{11}O_{17}/Al_2O_3$ [1], $Na_2Si_2O_5/SiO_2$ [3]; (ii) $NaAl_5O_8$ and $NaAl_{11}O_{17}$ [1, 2].

Customarily, the oxides present in pure form as solids are pulverized, optionally mixed with an inert electron conductor, e.g. Au, pressure-molded to form a pellet, and, as a compact molding or sintered body, brought into contact with the solid electrolyte. The electrode contact area (phase boundary II) is always that of two solids, which has the usual disadvantages that even with polished surfaces, only punctate contact will be established. Furthermore, the minimum achievable layer thickness, i.e. the spacing between the phase boundaries I and II is subject to a lower limit, as a result of which the oxygen potential at phase boundary I may differ from the oxygen potential at phase boundary II. However, the identity of the two potentials is a precondition for the validity of the equations (1a) and (1b).

PURPOSE OF THE INVENTION

The purpose of the invention is to provide a reference electrode for cation-conducting solid electrolytes which can be readily fabricated, is thin and ensures intimate contact with the solid electrolyte.

Essence of the Invention

According to the invention, said purpose can be achieved by one of the oxides being prepared as a hydrosol or organosol and thereby, in liquid form at room temperature or at only slightly elevated temperature, forming a solid film on the electrolyte.

Working Example

Figure 2:
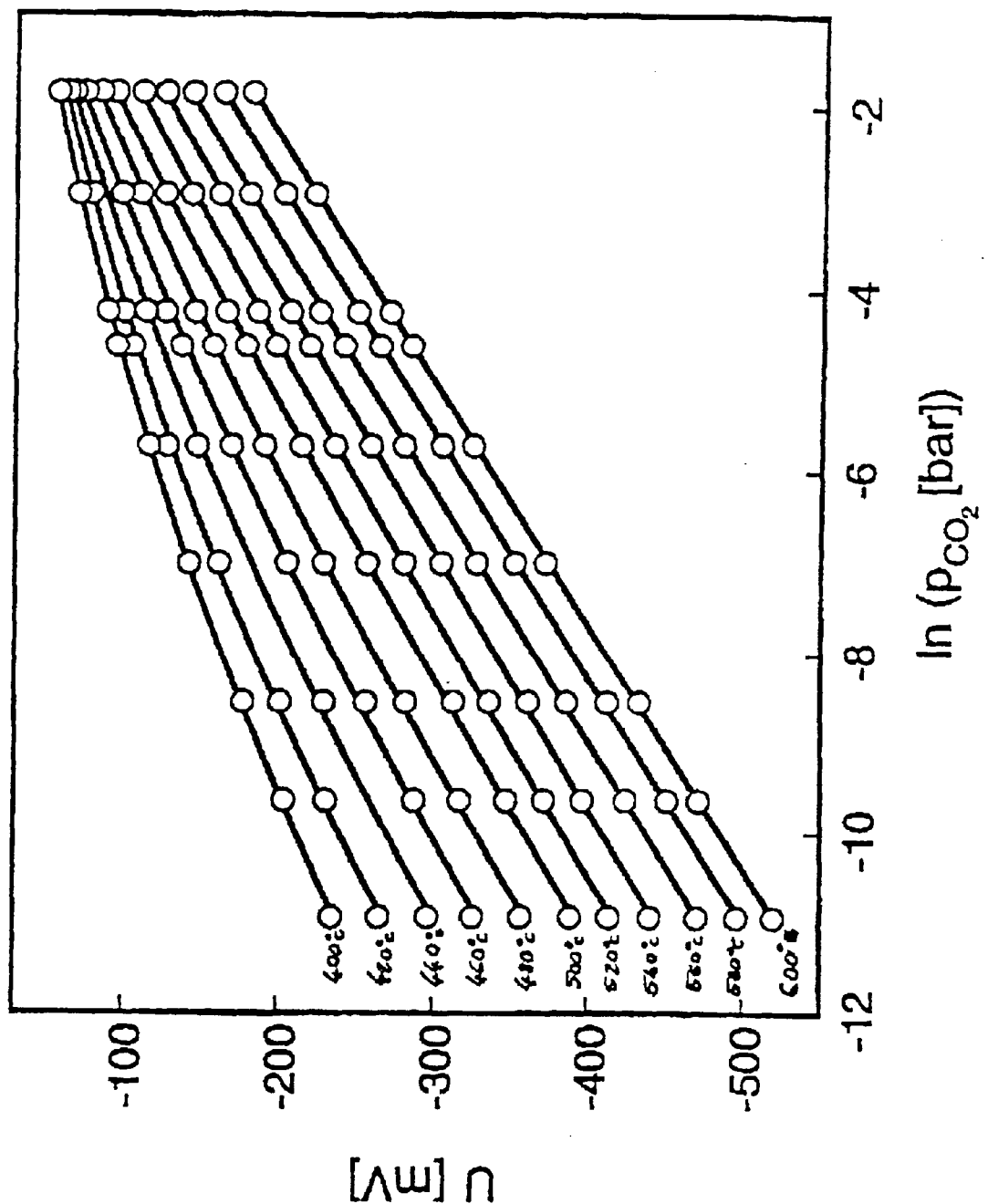

For example, Na and K silicate glasses can be dissolved at high pressure in water (water glass). A drop of such a water glass solution is applied to the solid electrolyte surface in such a way that a thin film is produced into which, prior to drying, a few grains of quartz sand ($SiO_2$) are introduced. At the same time, the water glass can be used to fix an Au mesh, which serves as pick-up electrode, to the surface of the solid electrolyte (see FIG. 1). FIG. 2 shows potential measurements of reference electrodes according to the invention at various temperatures.

Other systems are conceivable, mainly on the basis of silicates, e.g. sodium alumosilicates in equilibrium with pure $Al_2O_3$ and $SiO_2$, which can be prepared as sols and likewise be applied in liquid form.

References

[1] J. T. Kummer, Prog. Solid State Chem. 7 (1972), 141
[2] G. Rog, S. Kozinski, A. Kozlowska-Rog, Electrochim. Acta 28 (1983), 43
[3] H.-H. Möbius, P. Shuk, W. Zastrow, Fresenius J. Anal. Chem. 356 (1996) 221

What is claimed is:

1. A method for producing a reference electrode for galvanic cells having solid electrolytes containing at least one of a metal oxide or double oxide, the method comprising the steps of:
   (a) preparing a hydrosol or organosol from at least one oxide or double oxide;
   (b) applying the hydrosol or organosol of step (a) in liquid form to said electrolyte; and
   (c) forming a solid film of the hydrosol or organosol on said electrolyte,
   thereby providing an intimate contact of the at least one oxide or double oxide and the electrolyte without the addition of a binder to the hydrosol or organosol of step (a).

2. The method of claim 1, wherein a double oxide $Me^1_xMe^2_yO_z$ and (i) a metal oxide $Me^2_mO_n$ or (ii) a double oxide $Me^1_aMe^2_bO_c$ with a lower $Me^1$ content is present in the reference electrode.

3. The method of claim 2, wherein the double oxides are selected from the group consisting of sodium and potassium silicate glasses, and wherein these are prepared as a hydrosol and applied to the solid electrolyte surface as a thin film into which a few grains of quartz sand are introduced, and then drying the film with the introduced quartz sand.

4. The method of claim 1, wherein the double oxides are selected from the group consisting of sodium and potassium silicate glasses, and wherein these are prepared as a hydrosol and applied to the solid electrolyte surface as a thin film into which a few grains of quartz sand are introduced, and then drying the film with the introduced quartz sand.

* * * * *